United States Patent [19]

Engira

[11] Patent Number: 5,153,584
[45] Date of Patent: Oct. 6, 1992

[54] MINIATURE MULTILEAD BIOTELEMETRY AND PATIENT LOCATION SYSTEM

[75] Inventor: Ram M. Engira, Milwaukee, Wis.

[73] Assignee: Cardiac Evaluation Center, Inc., Milwaukee, Wis.

[21] Appl. No.: 670,483

[22] Filed: Mar. 14, 1991

Related U.S. Application Data

[63] Continuation of Ser. No. 325,765, Mar. 17, 1989, abandoned.

[51] Int. Cl.$^5$ .............................................. G08C 17/00
[52] U.S. Cl. ........................... 340/870.18; 340/825.36; 340/825.49; 340/573; 128/903
[58] Field of Search ............ 340/870.18, 825.31, 340/825.32, 825.36, 825.45, 825.34, 825.49, 825.54, 572, 573; 364/413.02, 413.03; 128/903, 419 P, 419 PG

[56] References Cited

U.S. PATENT DOCUMENTS

| | | | |
|---|---|---|---|
| 3,495,584 | 2/1970 | Schwalm | 128/696 |
| 3,639,907 | 2/1972 | Greatbatch | 340/870.09 |
| 3,768,017 | 10/1973 | Dillman et al. | 485/45 |
| 3,774,594 | 11/1973 | Huszar | 128/706 |
| 3,786,190 | 1/1974 | Pori | 370/123 |
| 3,815,109 | 6/1974 | Carraway et al. | 301/78 |
| 3,898,984 | 8/1975 | Mandel et al. | 128/696 |
| 3,921,621 | 11/1975 | Baessler | 128/736 |
| 3,943,918 | 3/1976 | Lewis | 128/640 |
| 3,953,848 | 4/1976 | Dillman et al. | 340/870.04 |
| 3,960,140 | 6/1976 | Buxton | 128/903 |
| 3,962,697 | 6/1976 | Vreeland | 340/870.14 |
| 3,986,498 | 10/1976 | Lewis | 128/903 |
| 4,063,410 | 12/1977 | Welling | 128/903 |
| 4,121,573 | 10/1978 | Crovella et al. | 128/640 |
| 4,156,867 | 5/1979 | Bench et al. | 340/825.49 X |
| 4,159,018 | 6/1979 | Brastad | 128/697 |
| 4,194,179 | 3/1980 | Malinouskas | 340/870.11 |
| 4,209,787 | 6/1980 | Freeny, Jr. | 340/991 |
| 4,217,588 | 8/1980 | Freeng, Jr. | 340/991 |
| 4,275,385 | 6/1981 | White | 340/825.49 |
| 4,281,664 | 8/1981 | Duggan | 128/696 |
| 4,319,241 | 3/1982 | Mount | 340/870.38 |
| 4,321,933 | 3/1982 | Baessler | 128/736 |
| 4,326,535 | 4/1982 | Steffel et al. | |
| 4,347,501 | 8/1982 | Akerberg | 340/573 |
| 4,356,486 | 10/1982 | Mount | 340/870.38 |
| 4,453,162 | 6/1984 | Money et al. | 340/870.39 |
| 4,503,862 | 3/1985 | Baessler | 128/736 |
| 4,531,526 | 7/1985 | Genest | 128/630 |
| 4,556,063 | 12/1985 | Thompson et al. | 128/419 PT |
| 4,562,840 | 1/1986 | Batina et al. | 128/419 PT |
| 4,593,273 | 6/1986 | Narcisse | 340/539 |
| 4,593,284 | 6/1986 | Clifford et al. | 340/870.18 |
| 4,598,275 | 7/1986 | Ross et al. | 340/573 |
| 4,658,831 | 4/1987 | Reinhard et al. | 128/419 PT |
| 4,686,988 | 8/1987 | Sholder | 128/419 PT |
| 4,837,568 | 6/1989 | Snaper | 340/825.49 |
| 4,958,645 | 9/1990 | Cadell et al. | 128/903 |

Primary Examiner—Donald J. Yusko
Assistant Examiner—Michael Horabik
Attorney, Agent, or Firm—Quarles & Brady

[57] ABSTRACT

A miniature multi-lead bio-telemetry and patient location systems includes one or more stationary location markers which transmit location data to an ECG unit worn by ambulatory patients. The electrocardiogram (ECG) unit monitors patient ECG data, a distress button and ECG unit status and combines this data with the location data received from one location marker and retransmits this combined data to a stationary receiver which may display the ECG data the system status data and the location data.

9 Claims, 14 Drawing Sheets

MINIATURE MULTILEAD BIOTELEMETRY AND PATIENT LOCATION SYSTEM

This is a continuation of application Ser. No. 07/325,765, filed Mar. 17, 1989 now abandoned.

BACKGROUND OF THE INVENTION

The field of the invention relates to bio-telemetry in general and specifically to bio-telemetry systems capable of providing patient location information.

Bio-telemetry systems are now widely used to monitor patients in cardiac care and rehabilitation centers. Most existing telemetry monitors are capable of monitoring only cardiac rhythm and do not possess the requisite bandwidth and other features essential for an accurate analysis of a wide variety of cardiac arrhythmias. Development of a biotelemetry system suitable for providing a diagnostic quality multilead electrocardiogram (ECG) signal is highly desirable. Such a system would then permit use of modern real time analyses arrhythmia monitors on ambulatory patients.

Prior bio-telemetry systems are mostly single ECG channel systems. For example, the one disclosed in U.S. Pat. No. 3,953,848. A number of multi-lead ECG telemetry systems have also been described. Examples are those disclosed in U.S. Pat. Nos. 3,962,697; 3,815,109 and 4,356,486. These attempts are useful contributions to the field but the radio frequency bandwidth required by these systems does not permit monitoring of a large number of patients in the same hospital.

In an event of a detected serious arrhythmic episode, a patient must be located quickly so that life saving measures can be initiated. Thus, it is also desirable to have an automatic patient location capability in the monitoring system.

U.S. Pat. No. 4,593,273 discloses an out-of-range personnel monitor and alarm. Although this system may sound an alarm if a patient walks out of range, it does not help hospital personnel in locating the patient. It also implicitly limits the freedom of the patient to move about.

Further, the existing systems do not readily adapt to the transmission of other useful information, such as patient temperature, patient distress, pacer spikes, blood oxygen, electrodes and the status of the equipment itself.

SUMMARY OF THE INVENTION

The present invention relates to a multi-lead ECG telemetry systems, using PCM, to provide a diagnostic quality signal suitable for real time arrhythmia analysis monitors. More specifically the invention relates to an ECG telemetry system incorporating a patient location system which comprises one or more stationary location markers may transmit a presettable location code indicating the location of said location marker. An identification unit comprising a patient carried ECG transmitter unit communicates with the location marker via a low power communication link whose range defines a bounded space. The location code for a location marker and a patient identification signal produced by the patient identification unit is transmitted to a stationary receiver only when the location marker is in communication with the patient identification unit. The stationary receiver receives the location code and the patient identification signal so as to provide information as to the location of the patient wearing the patient identification unit.

Accordingly, one object of the invention is to permit hospital personnel to locate, ambulatory patients experiencing arrhythmic episodes rapidly.

A further object of the invention is to provide a method of monitoring physiological status of the patient. The patient carried ECG transmitter unit contains multilead ECG monitoring circuitry. The physiological signals from this monitoring circuitry are combined with the patient identification information. The stationary receiver includes circuitry to decode the physiological signals to provide real-time monitoring of the physiological signals.

It is another object of the invention is to prevent interference between the retransmitted signals of a number of ECG transmitter units operated within the same institution each monitoring a number of ECG signals. The physiological signals and location code are combined by using pulse code modulation (PCM). This allows narrow band Very High Frequency (VHF) channels for each patient, consequently allowing a large number of patients to be monitored on unused television (TV) frequency channels. The patient identification information is determined by the particular frequency channel used.

It is another object of the invention to allow the patient to simultaneously indicate his or her distress and location to a remote station. Each patient carried ECG transmitter unit contains a distress button that signals the stationary receiver of the patient's activation of that button. The stationary receiver also indicates the patients location by means of the location markers as described above.

It is a further object of this invention to efficiently combine high bandwidth physiological signals with low bandwidth circuit status data and location code data, with a minimum increase in bandwidth. The combined information is transmitted in a stream of data frames. Physiological data is transmitted in every frame, but location data and status data is spread among the frames according to its relative data rate. Therefore, the bandwidth of the system required to send physiological data and status and location data need not be markedly increased over that required by the physiological data alone.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

DESCRIPTION OF THE PREFERRED EMBODIMENT

Figure 1:
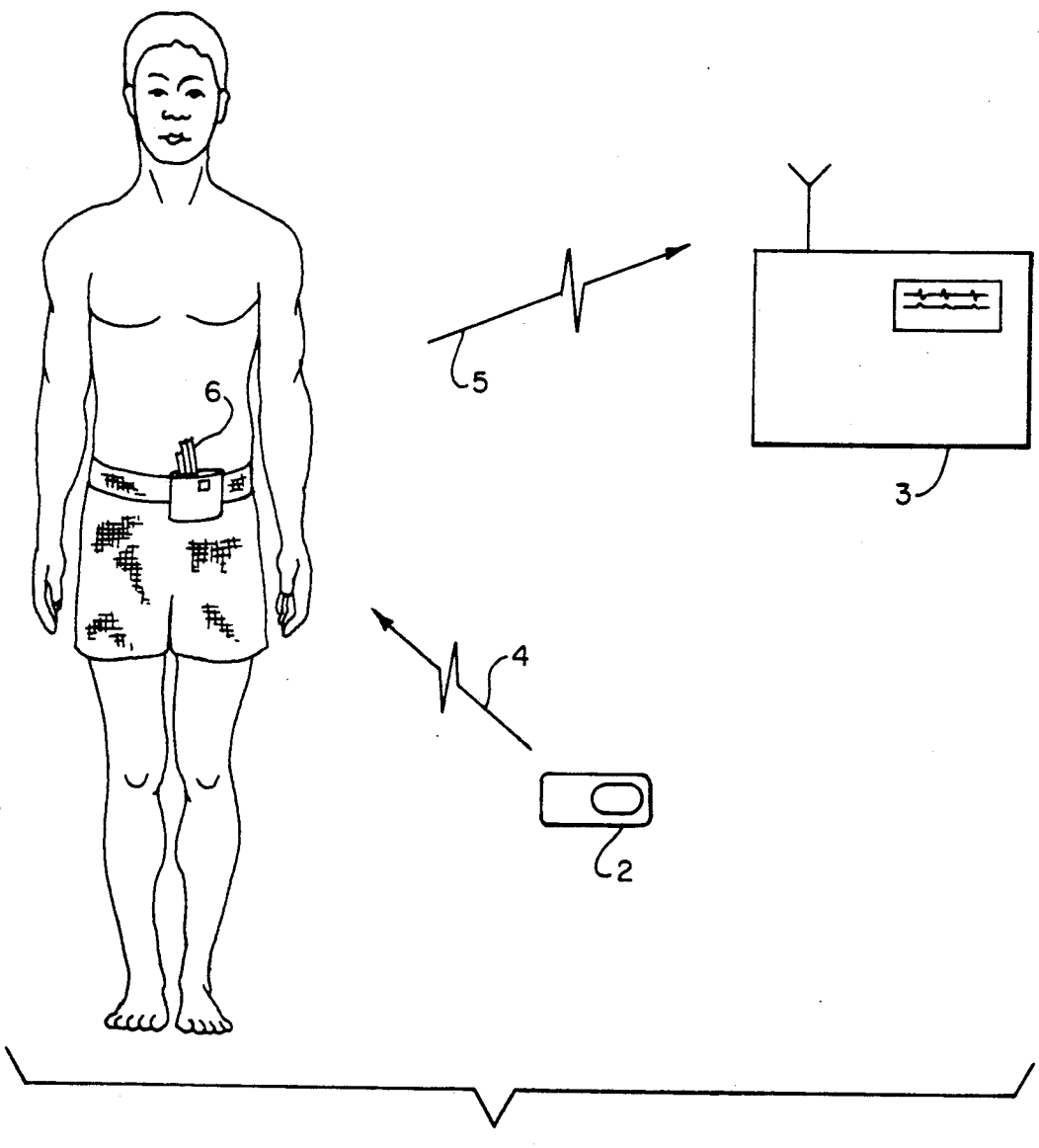
FIG. 1 is a perspective view of a stationary location marker, a patient worn ECG transmitter unit and a central monitoring station.

Referring to FIG. 1, an ECG transmitter unit 1 is attached to the patient's clothing and electrically connected to the patient's body through ECG electrodes 6. Location markers 2 are installed at prominent locations (i.e. corridors, doors, etc.). Each location marker 2 continuously transmits a unique location code using a pulse code modulated infrared beam 4 of limited strength forming a low power link. The strength of this signal defines a bounded space associated with one location code. The patient carried ECG transmitter unit 1 is provided with a means to receive this infrared beam 4 provided that the strength of the beam is above a given power level. By limiting the power level of the infrared location markers 2 and by installing the markers far enough from each other, a number of bounded spaces may be established and it may be ensured that the patient carried ECG transmitter unit 1 receives a location code from only the nearest location marker 2 within a given bounded space.

The ECG transmitter unit 1 combines the location code with digitized ECG and status data and transmits the same on a pulse code modulated (PCM) radio frequency signal 5, which is received by a stationary receiver 3. The carrier frequency of the radio frequency signal is unique to the ECG transmitter unit 1 and therefore identifies that ECG transmitter from others. Thus the ECG transmitter unit 1 serves as a patient identification unit and the carrier frequency of its transmission carry patient identification information.

The status data, also transmitted in the PCM signal, will be described in detail below. The stationary receiver 3 decodes, separates and displays the multi-lead ECG data, patient location data, and the system status.

The Location Marker

Figure 2:
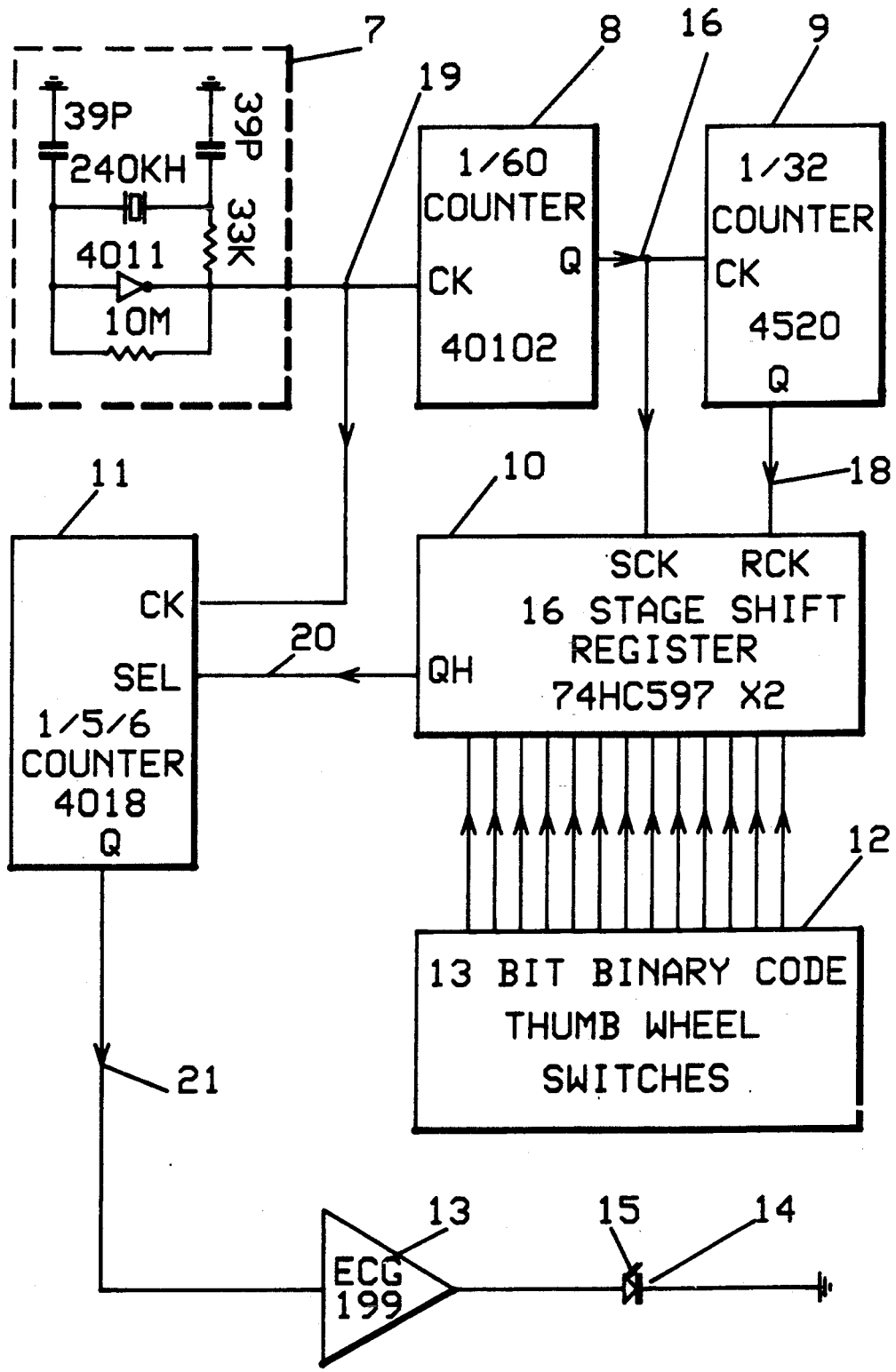
FIG. 2 is a schematic diagram of the stationary location marker shown in FIG. 1.
Figure 3:
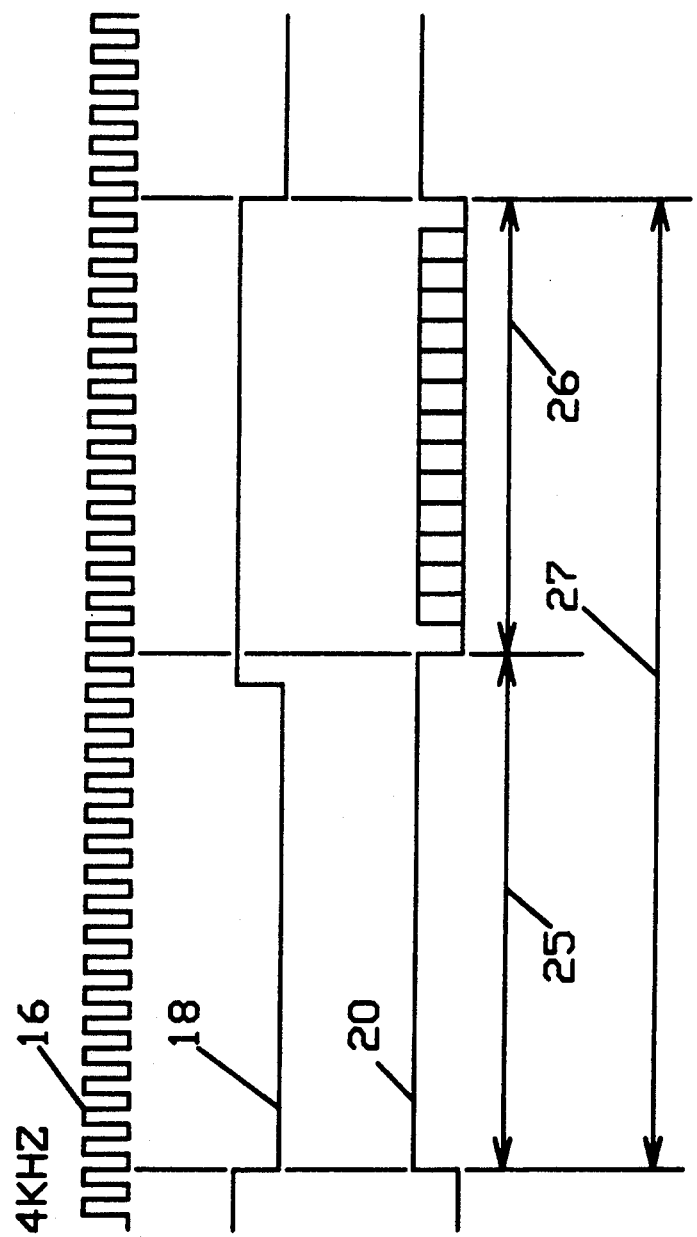
FIG. 3 is a timing diagram of the signal generated by the stationary location marker of FIG. 2.

Referring to FIGS. 2, the location marker 2 includes a crystal controlled oscillator 7 which generates a 240 kHz clock signal 19 that is divided by a counter 8 to produce a 4 kHz S-clock signal 16. This 4 kHz clock signal 16 is further divided by the counter 9 to generate the R-clock signal 18. A parallel-in-serial-out shift register 10 is wired to load a 13-bit location code from the thumbwheel switch 12. The location code is arbitrary and set by the user to uniquely define the location of the bounded space around the location marker. Together with S-clock and R-clock inputs 16 and 18, shift register 10 produces a serial data signal 20. Referring to FIG. 3, the serial data signal 20 includes a 17-bit leader byte 25 used by the system for synchronization as is generally understood in the art. Following the 17 bit leader byte 25 is a 15-bit long data string 26 including a logic low start, a 13-bit location data word and also a logic low stop bit. The 13-bit location data word is selected by setting of the thumbwheel switch 12 and allows more than eight thousand (8000) locations to be identified by the location marker 2. The length of the location data word may be varied to suit the requirements of the hospital. Referring again to FIG. 2, a counter/divider 11 divides the 240 kHz clock signal 19 by five when the serial digital signal 20 is high and by six when the serial digital signal 20 is low. Thus, the output signal 21 from the counter divider 11 equals the 240 kHz clock signal 19 frequency shift key (FSK) modulated by the location code set by the thumbwheel switch 12. Output signal 21 drives an output amplifier 13 which, in turn, drives infrared light emitting diode (LED) 14 to produce an infrared beam carrying location code information. The power of the infrared beam is such as to confine the location code signal to the area of a single room or lobby of the hospital.

ECG Transmitter Unit

Figure 4:
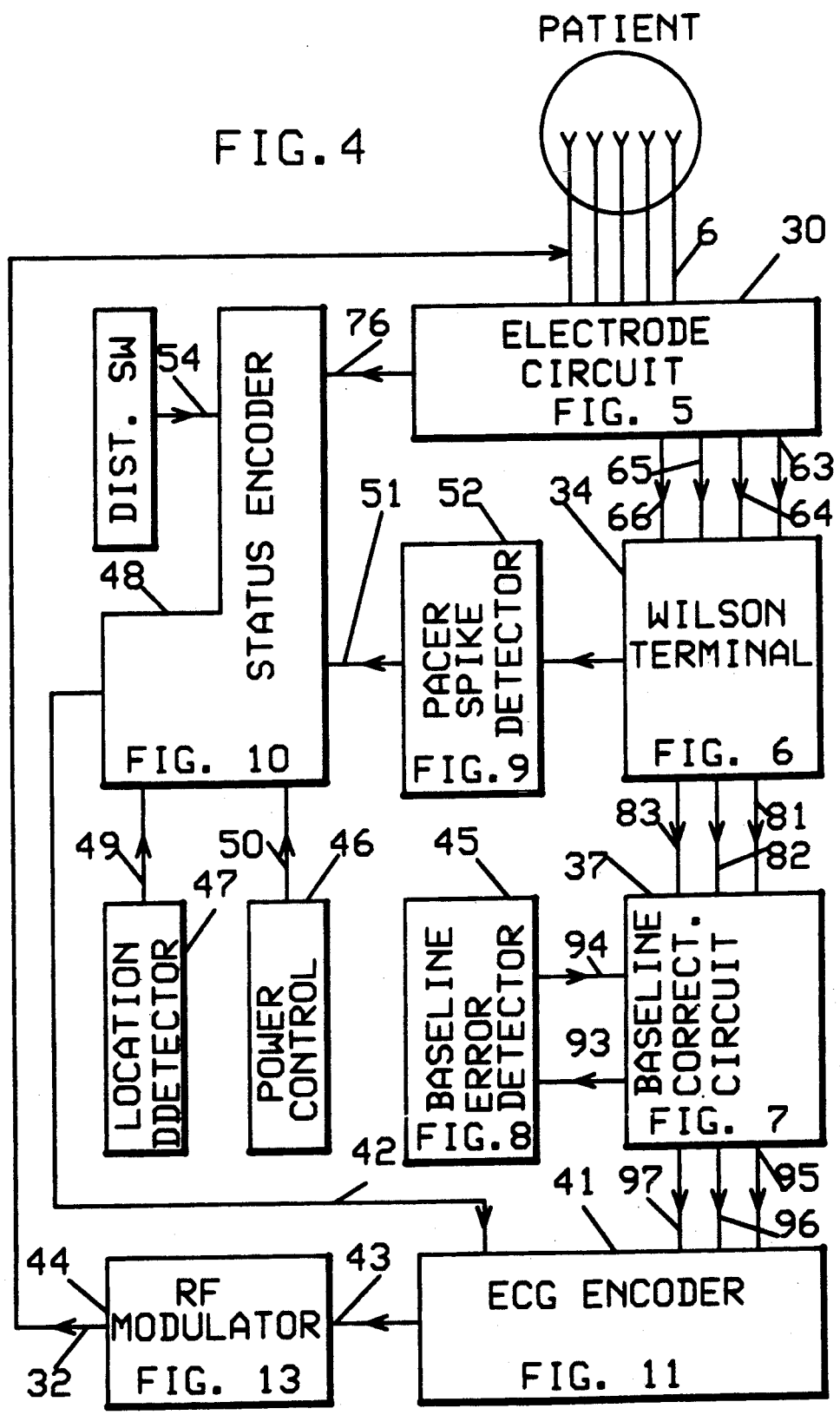
FIG. 4 is a block diagram showing the ECG transmitter unit shown in FIG. 1.
Figure 5:
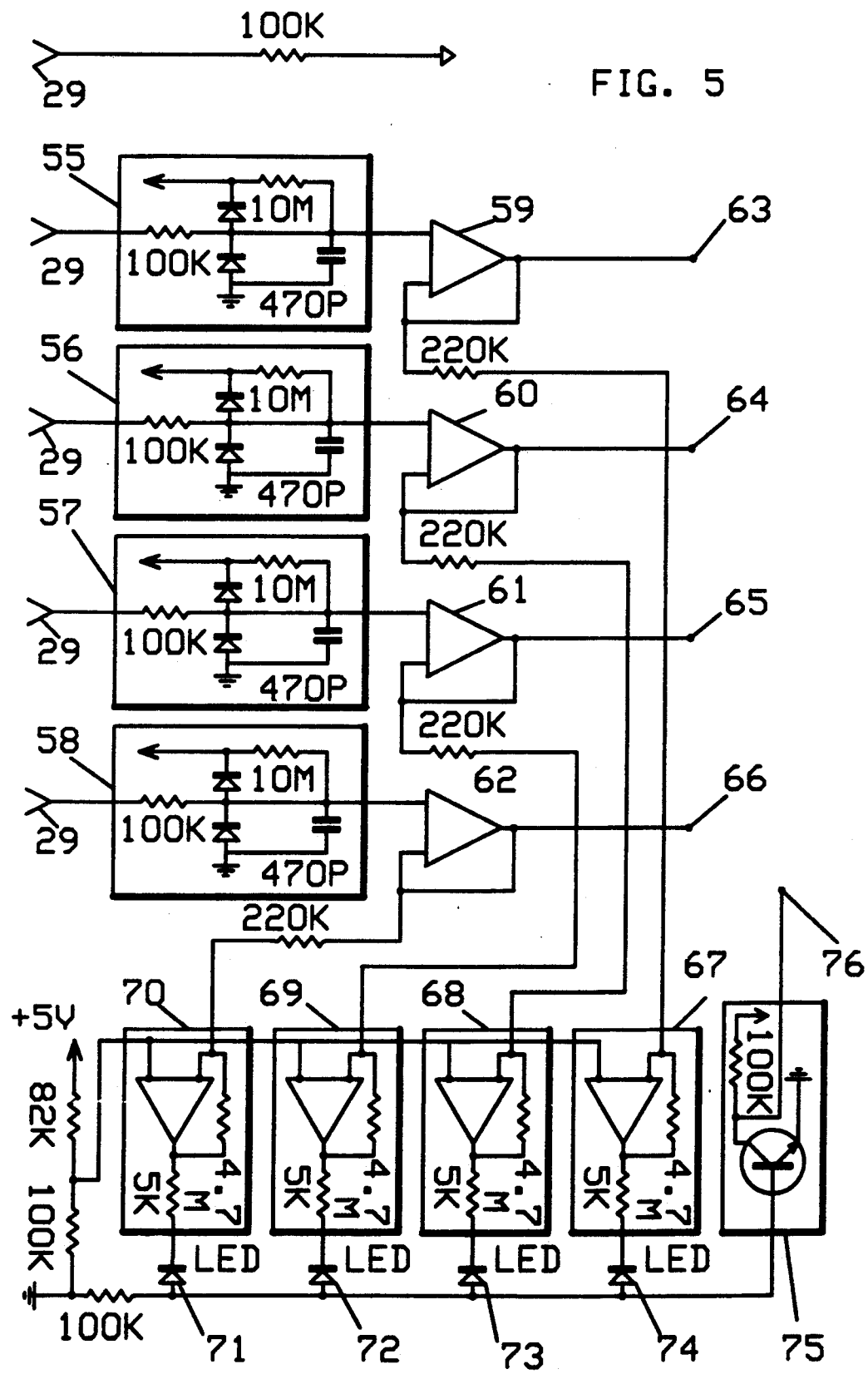
FIG. 5 is a schematic diagram of the electrode circuit of the ECG transmitter unit as shown in FIG. 4.

Referring to FIG. 4, a patient is connected to the ECG transmitter unit 1 through electrocardiograph electrodes 6. The electrode circuit 30, shown in detail in FIG. 5, contains wave trap RC filters and diode protection circuits 55 to 58, to stop RF signals from reentering the unit, and to limit current in-rush during patient defibrillation. Block 30 also contains electrode monitoring circuitry consisting of analog buffers 59 to 62 and comparator drivers 67 to 70 as shown in FIG. 5. This circuit monitors electrode fall-off condition. If an electrode fall-off is detected, it turns on corresponding LED indicators 71 to 74. The fall-off condition is indicated by an increase in the impedance of the electrodes. Logic OR circuit 75 generates an electrode fall-off alarm status signal 76. Buffered ECG signals 63 to 66 go to the Wilson terminal block 34.

Figure 6:
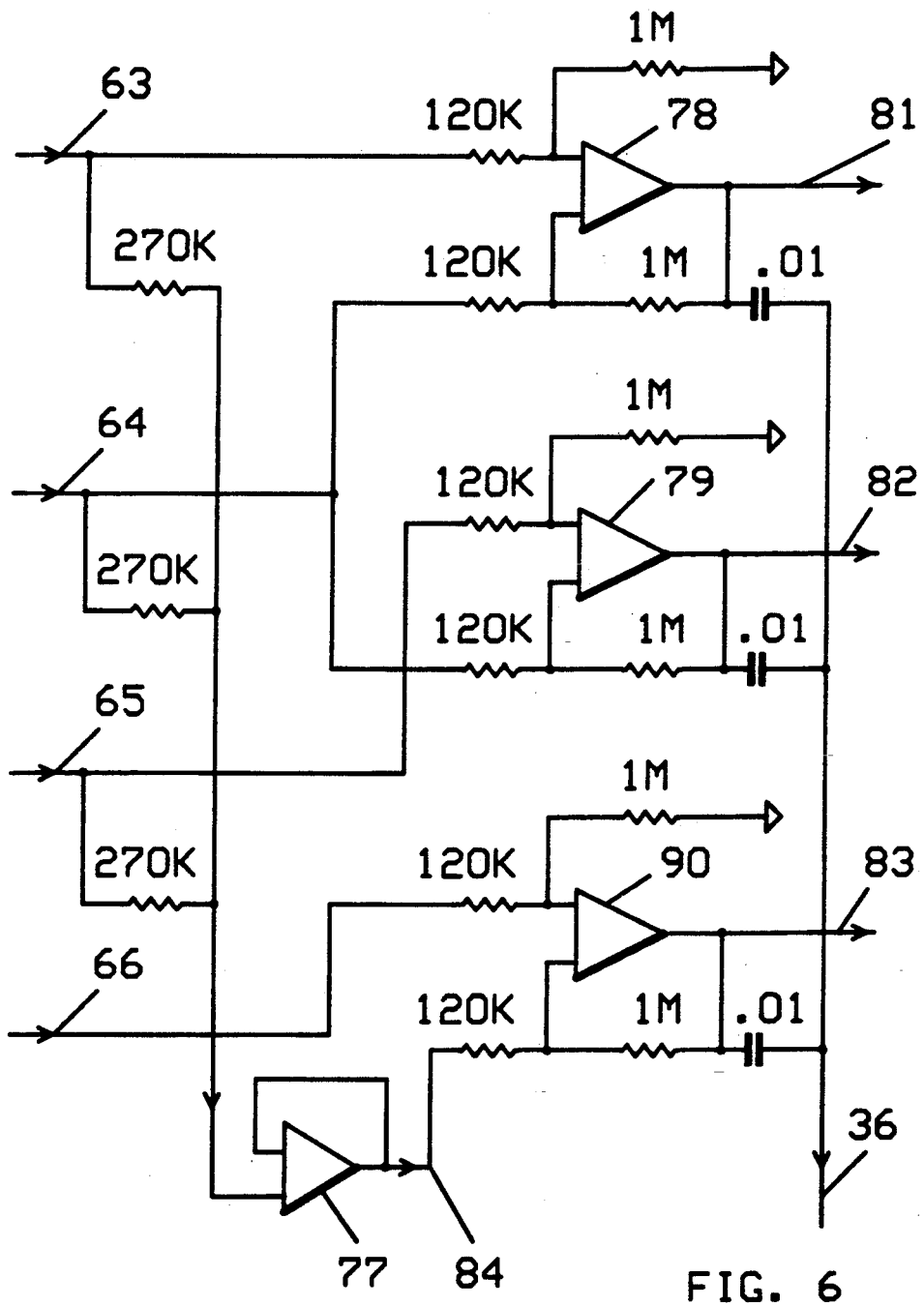
FIG. 6 is a schematic diagram of the Wilson Terminal and standard lead amplifiers of the ECG transmitter unit as also shown 4.

Wilson terminal block 34 contains circuits shown in FIG. 6. Averaging amplifier 77 computes a Wilson ground 84 from the three limb lead inputs 63, 64 and 65. The difference amplifier 80 uses Wilson ground 84 and buffered ECG chest lead signal 66 to compute a standard ECG V lead 83. Difference amplifiers 78 and 79 use buffered ECG limb lead signals 63, 64 and 65 to compute standard ECG signals lead I 81, and lead II 82 and V lead 83. Signals 81, 82 and 83 are capacitively coupled to pacer input signal 36 for pacer spike circuits.

Figure 7:
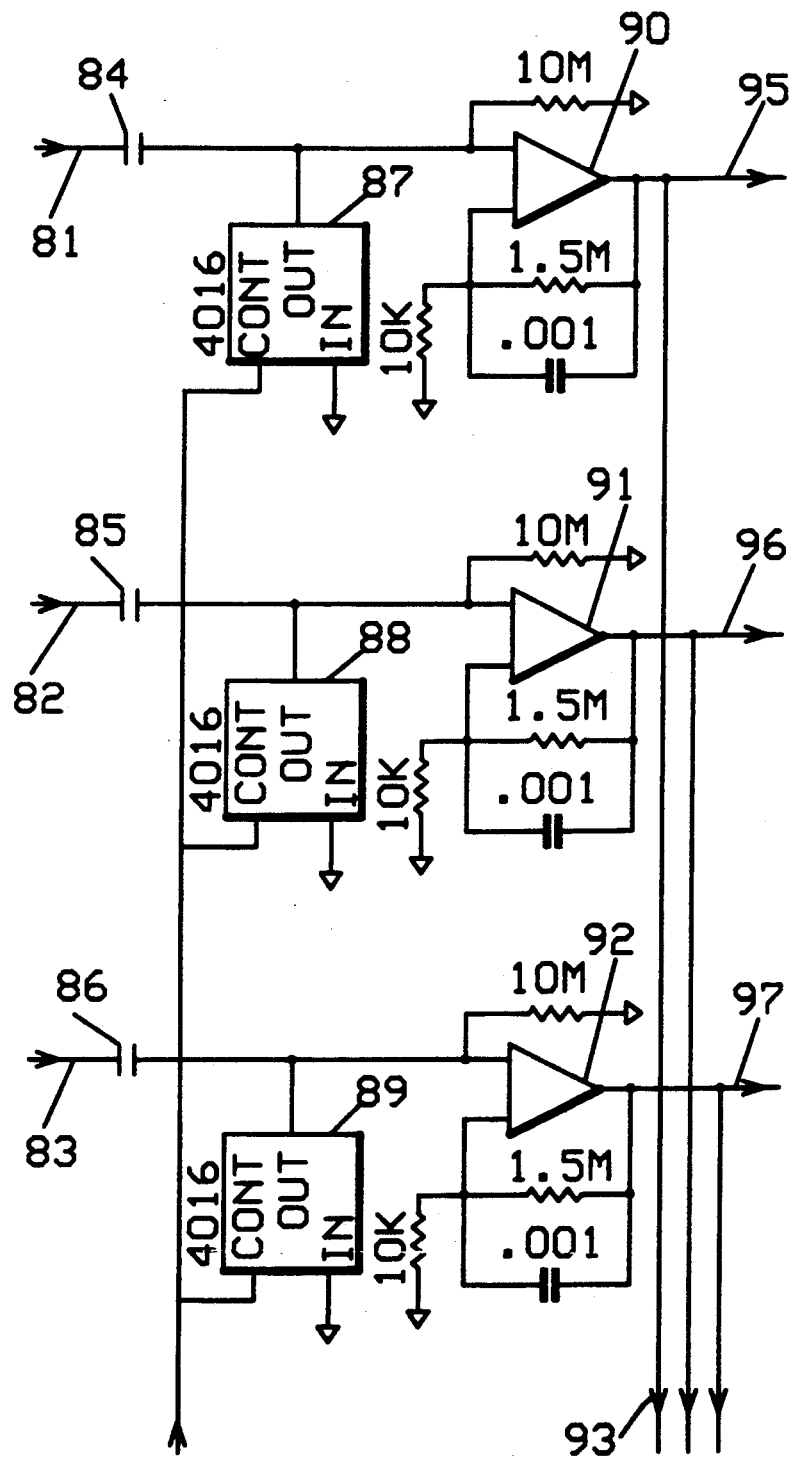
FIG. 7 is a schematic diagram of the ECG amplifiers and baseline correction switches of the ECG transmitter unit shown in FIG. 4.

Block 37 of FIG. 4 contains ECG amplifiers and baseline correction circuits shown in detail in FIG. 7. Standard ECG signals 81, 82 and 83 are coupled through capacitors 84, 85 and 86 to the ECG amplifiers 90, 91 and 92 to produce signals 95, 96 and 97. Analog switches 87, 88 and 89 ground amplifier inputs whenever a baseline correction command pulse 94 is received from the baseline error detection circuit 45 described below.

Figure 8:
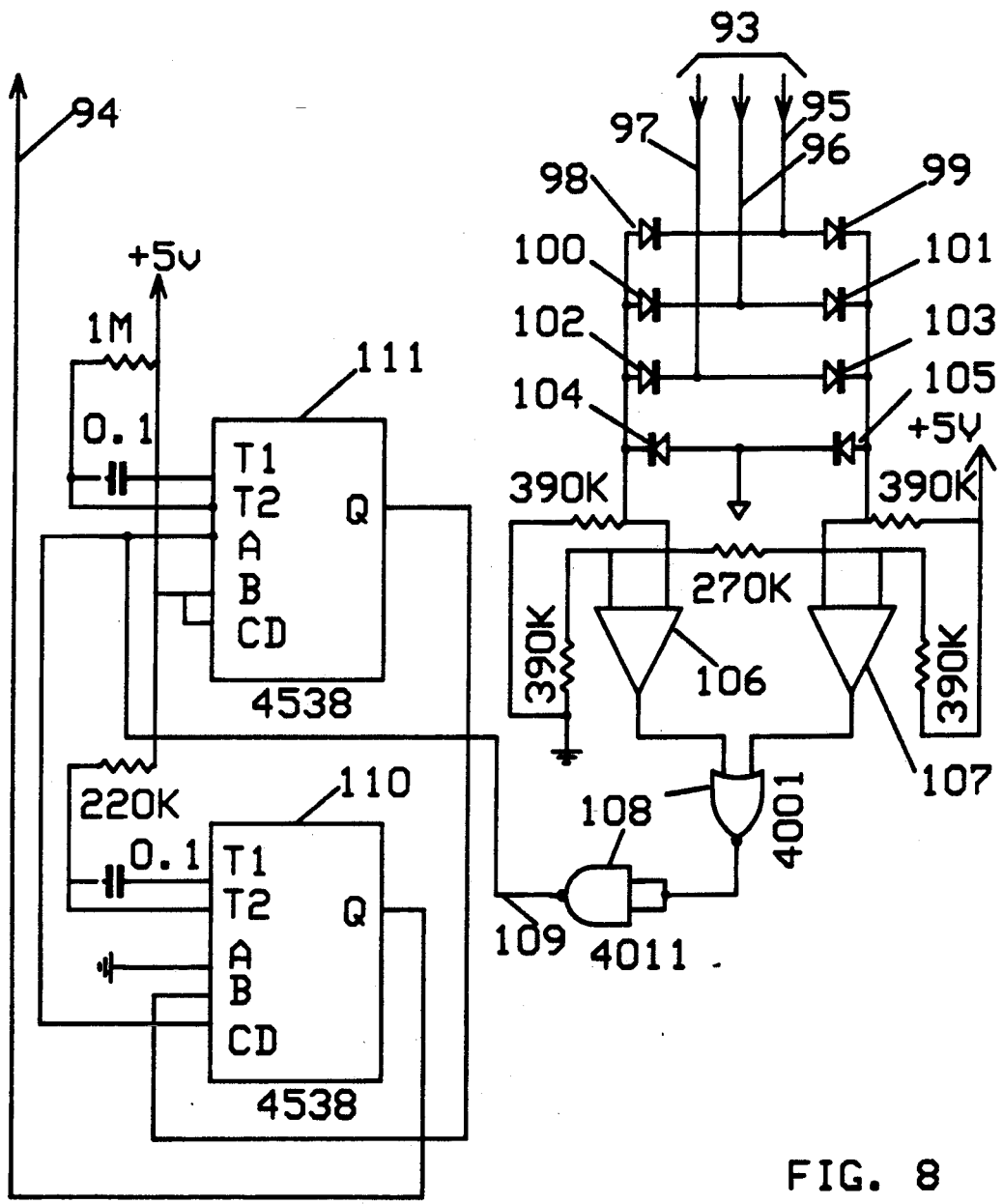
FIG. 8 is a schematic diagram of the baseline error detection circuits of the ECG transmitter unit as shown in FIG. 4.

The baseline error detection circuit 45, shown in detail in FIG. 8 receives amplified ECG signals 93 (comprised of 95, 96 and 97). Window comparators consisting of diodes 98 to 105 and difference amplifiers 106 and 107 and OR gate 108 generate a baseline error signal 109. The baseline error signal 109 is generated whenever the baseline of 95, 96 and 97 wanders outside the prescribed threshold of the window comparators of approximately 1.4 volts. Discriminator circuit consisting of monostable multivibrators 110 and 111 inhibit generation of correction pulse 94 unless the baseline error persists beyond a prespecified period of 5 seconds. The correction pulse 94 is used by the baseline correction circuit 37 as explained above.

Figure 9:
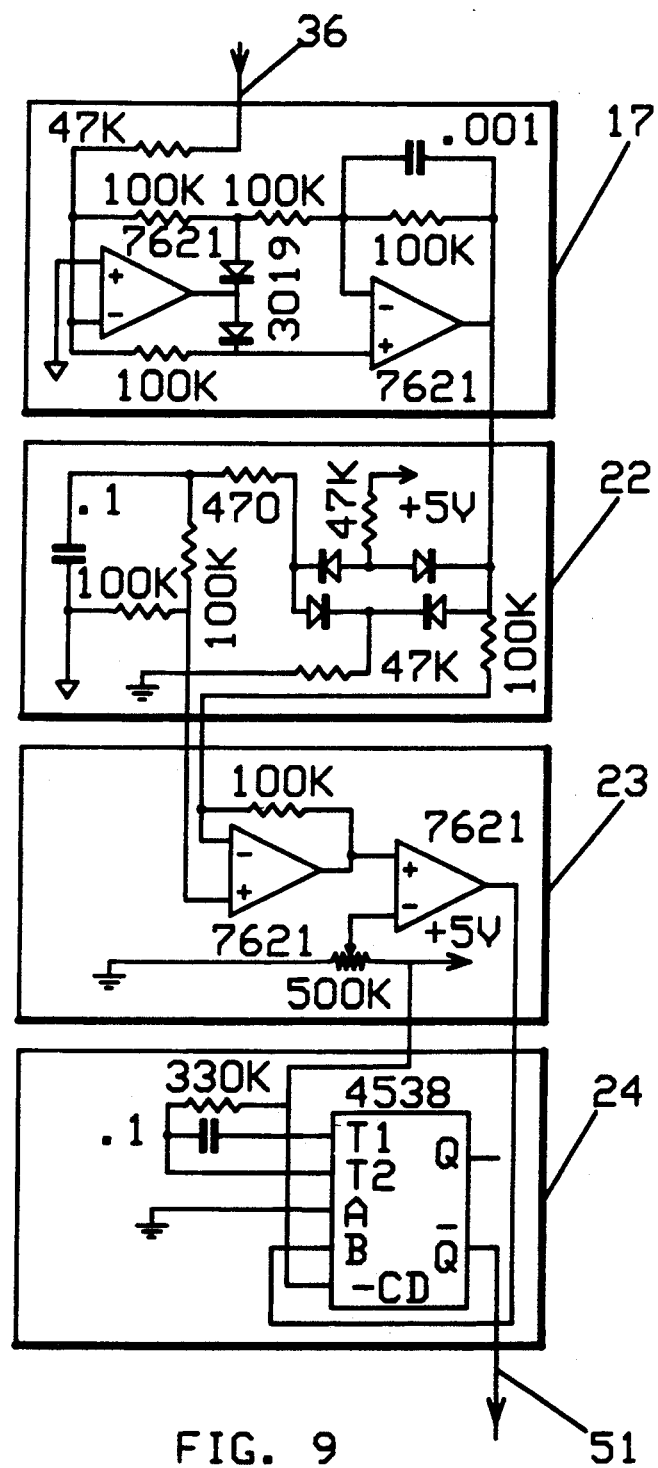
FIG. 9 is a schematic diagram of the pacer spike detector circuit of the ECG transmitter unit as shown in FIG. 4.

Block 52 of FIG. 4 contains pacer spike detector circuit. The ECG signal measured from patients with pacemakers includes a pacer spike. It is clinically important to see that each pacer spike triggers the appropriate ECG response. The frequency content of the pacer spike is much higher than that of the ECG signal hence the pacer spike is first detected and filtered from the combined pacemaker plus ECG signal. If a pacemaker pulse is detected, a digital pacer status pulse is generated which is sent separately to the stationary receiver 3 and recombined with the ECG waveform. The pacer spike detector circuit is shown in detail in FIG. 9. Pacer signal 36 from Wilson terminal 34 is passed through an absolute value circuit 17. Output of 17 is passed through a slew rate filter circuit 22 and a difference amplifier 23. Pacer spike output of 23 is passed through a pulse stretcher monostable multivibrator 24 to generate a pacer status pulse output 51.

Figure 10:
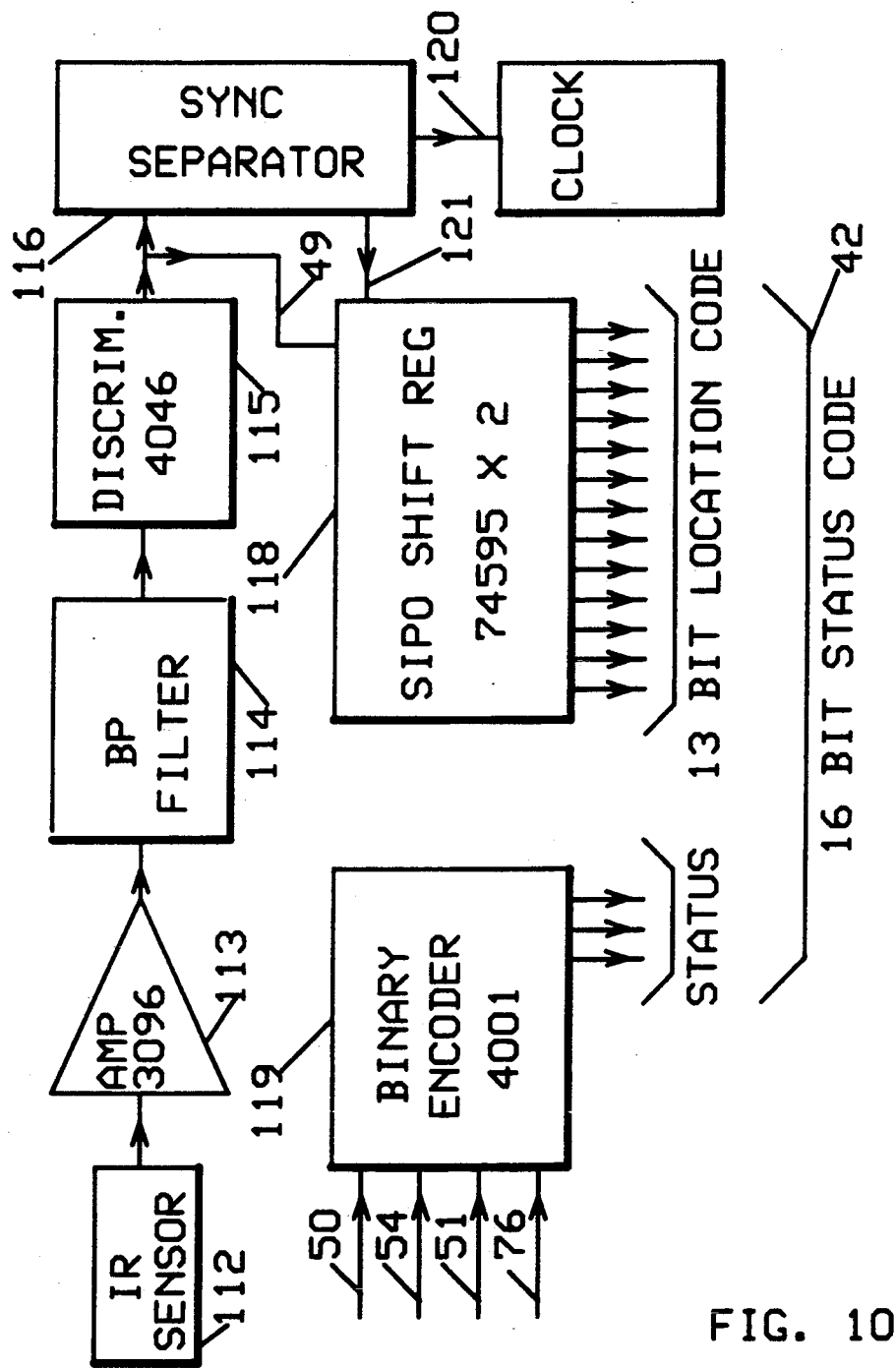
FIG. 10 is a schematic diagram of location code detector and the status encoder circuits of the ECG transmitter unit as shown in FIG. 4.

The signal 76 from electrode monitoring circuit, 51 from the spacer spike detection circuit, 54 from distress switch, and 50 from power control circuit comprise the status code which is combined with the location code and transmitted with the ECG signals by the status encoder shown in FIG. 10. Binary encoder 119 collects these signals into a 3-bit status code.

A location code detection circuit is also shown in FIG. 10 block 47, and consists of an infrared detector 112 that detects presence of an infrared location code radiated by a stationary location marker. Amplifier 113 amplifies output of the sensor that passes through filter 114 and a discriminator 115 to generate a serial PCM location code data 49. Sync separator circuit 116 uses data 49 together with clock signal 120 to produce a shift register clock signal 121. The serial-in-parallel-out shift register collects a 13-bit location code which is added to a 3-bit status code generated by the encoder 119 to produce a final 16-bit system status word 42.

Figure 11:
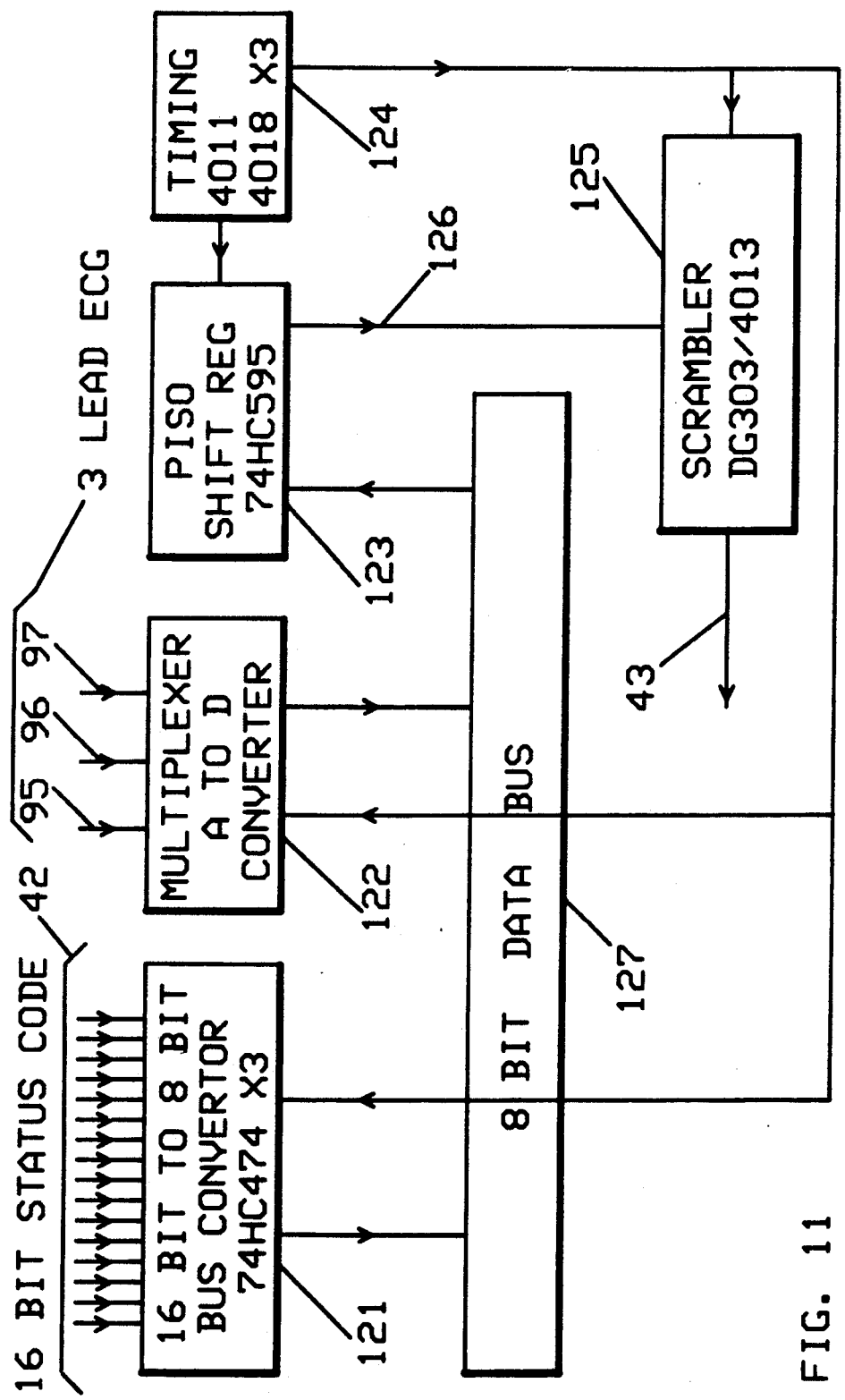
FIG. 11 is a schematic diagram of the ECG encoder circuits of the ECG transmitter unit as shown in FIG. 4.

The ECG encoder shown generally in block 41 of FIG. 4 receives analog ECG data 95, 96 and 97 from baseline correction circuit 37, and 16-bit status word 42 from status encoder 48 described above. A detailed schematic diagram of the ECG encoder is shown in FIG. 11. Sixteen-bit status word 42 is converted to two multiplexed 8-bit words 200 and 202 representing the most significant bits and the least significant bits of the sixteen bit status word 42 respectively. This conversion is performed by the 16 to 8 bus converter 121. The three lead ECG signals 95, 96 and 97 are multiplexed and converted to three 8-bit digital data words 95′, 96′, and 97′ by the multiplexer converter 122 and concatenated with the 8-bit status bytes by the parallel-in-serial-out shift register 123 which serializes this 8-bit data as will be described below. The serialized data 126 from shift register 123 is sent to scrambler circuit 125 which "scrambles" the data stream to eliminate long strings of logical "ones" or logical "zeros" to improve transmission efficiency as is well understood in the art. The scrambled signal 43 is input to the RF modulator 44.

Figure 12:
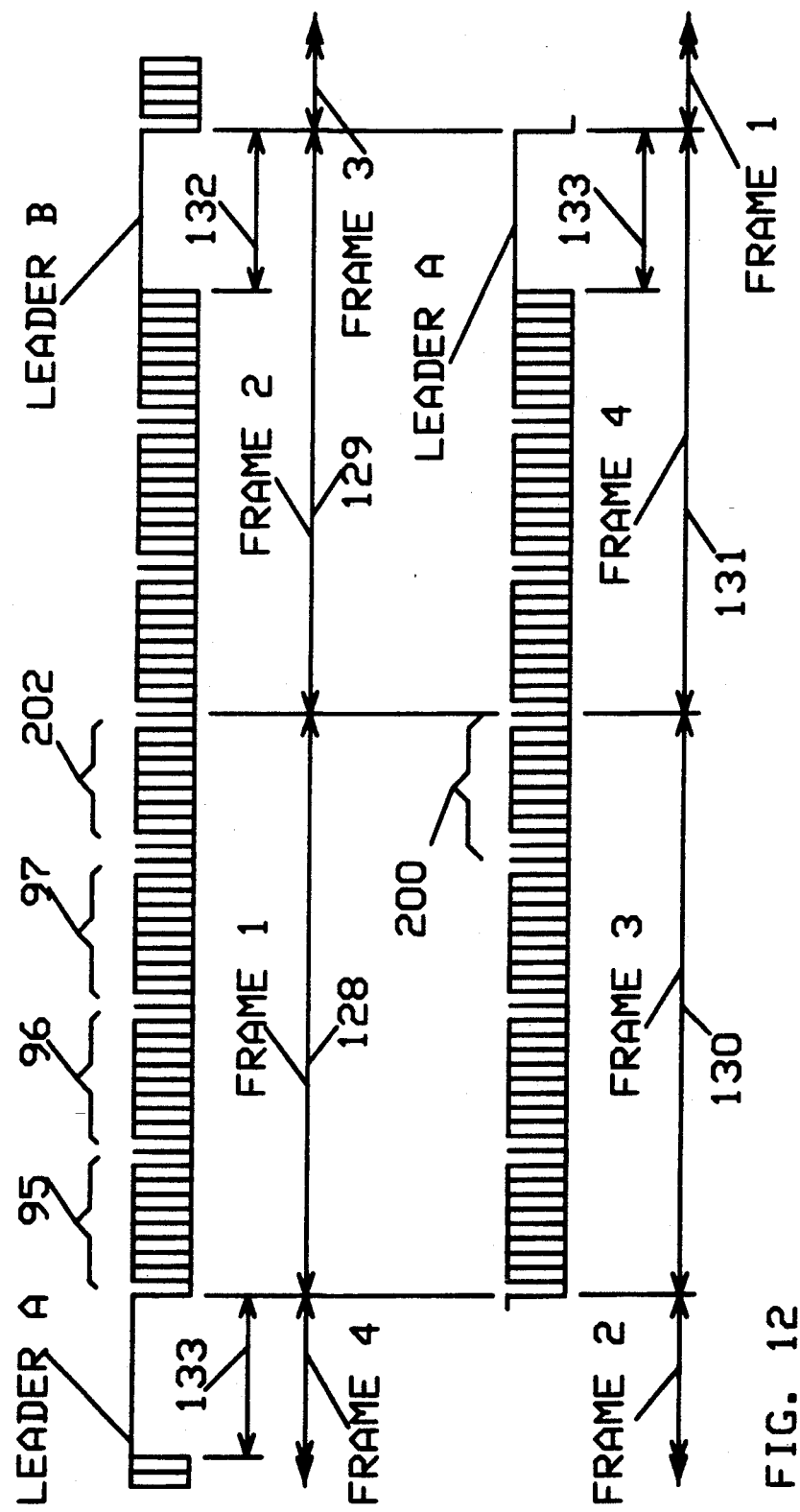
FIG. 12 is a timing diagram showing the PCM data encoding protocol of the retransmitted signal of the present invention.

The method of combining the 16 bit system status word 42 and the ECG signals will now be described. Referring to FIG. 12, data are grouped in frames of 40-bit length. A set of four frames comprises a cluster. The four frames 128–131 of each cluster are numbered 1 to 4 as shown in FIG. 12. Each frame of a cluster starts with a 10-bit data string consisting of an 8-bit data byte from ECG lead one plus one start and one stop bit. This is followed by two similar 10-bit data strings from ECG leads two and three. Start bits of all ECG lead data strings are low. Stop bits of leads one and two are also always low. Stop bits of the third lead are low for frames one and three, and high for frames two and four. The thirty-first bit of each frame is low for frames one and three, and high for frames two and four. The thirty-second through thirty-ninth bits represent lower and higher order status bytes from 16 bit to 8 bit converter 121 in frame one (1) and three (3) respectively. These two bytes are followed by a low stop bit. Bits 30 to 40 in frames two and four are always high and form 11-bit long leader bytes used by the receiver to extract synchronization information. The preferred embodiment of the invention transmits 50 data clusters per second. That is equivalent to 200 frames per second. An important advantage of this protocol is the efficiency with which high frequency ECG data is combined with slow varying status and location data without increasing serial data rate substantially above that required by the ECG data alone.

Figure 13:
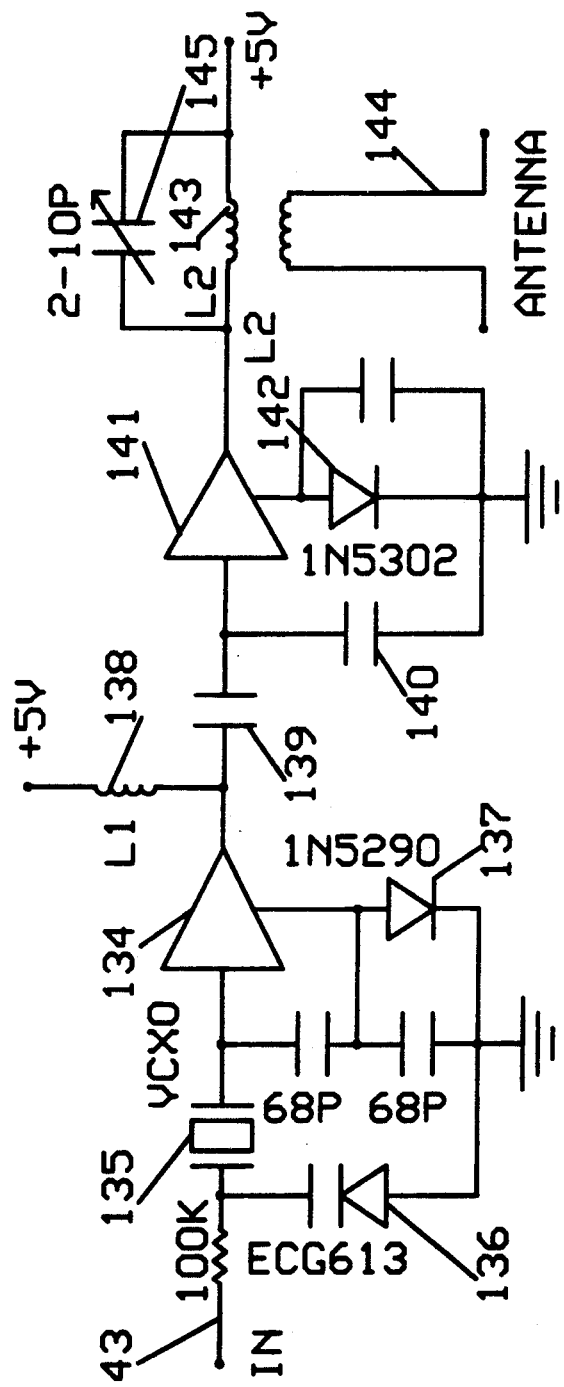
FIG. 13 is a schematic diagram of the radio frequency circuit used in the ECG transmitter unit as shown in FIG. 4.

Block 44 in FIG. 4 shown in detail in FIG. 13 represents the RF modulator stage of the transmitter. The voltage controlled crystal oscillator consists of an amplifying device 134, a quartz crystal of one-fourth the RF channel frequency 135, a varactor diode 136, and a current regulating diode 137. Output of 134 is tuned by an inductor 138 and capacitors 139 and 140, to the second harmonic of the crystal 135. Capacitors 139 and 140 also provide impedance matching to the output stage frequency doubler amplifier 141. Current regulator diode 142 and 137 provide added stability in frequency and power. The output of 141 is tuned by inductor 143 and capacitor 145 and coupled to the antenna circuit 144. Two of the ECG electrodes are used to form the antenna.

Figure 14:
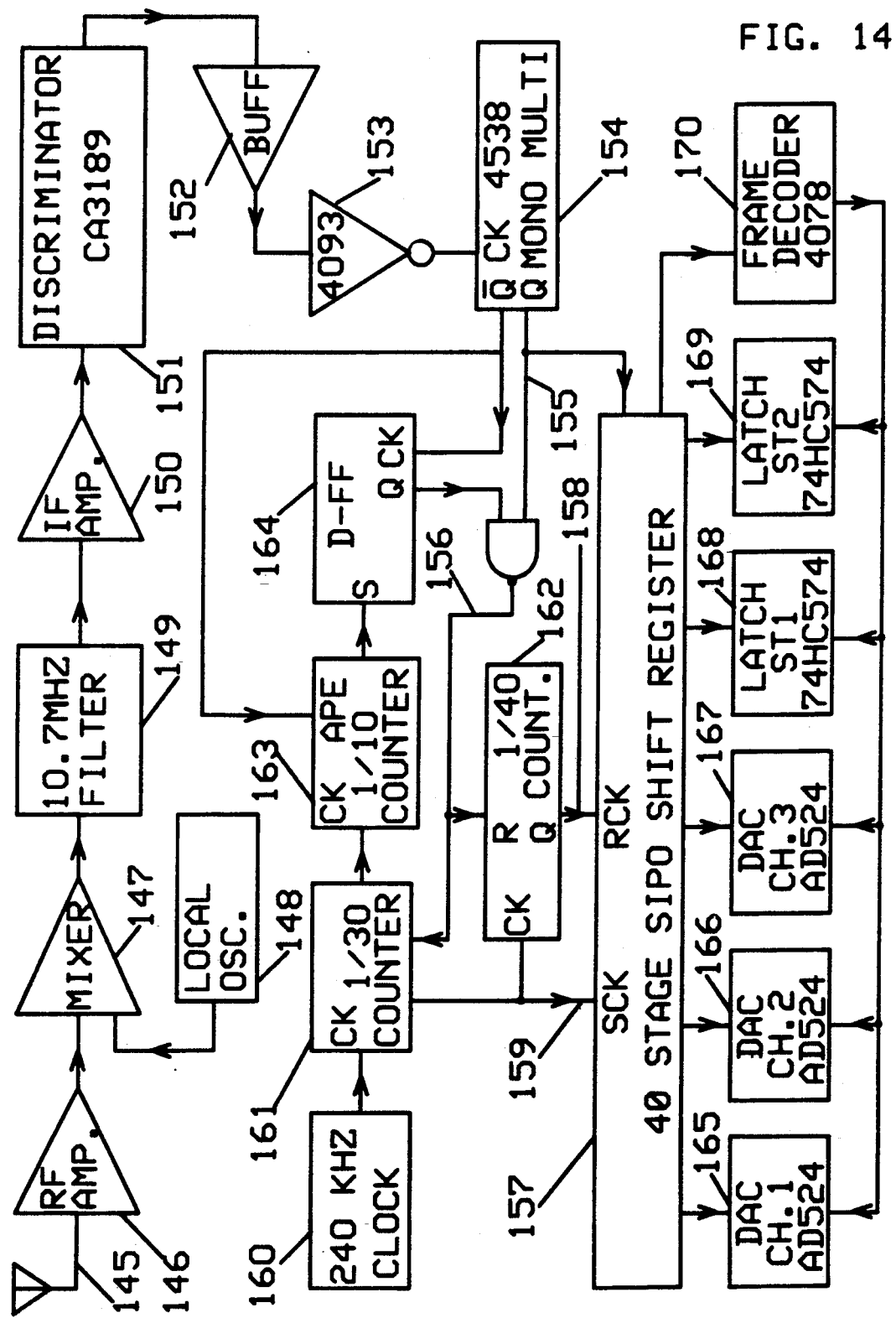
FIG. 14 is a functional block diagram of the stationary receiver unit shown in FIG. 1.

Referring to FIG. 14, the receiving antenna 145 of stationary receiver 3 feeds RF amplifier 146 tuned to the RF channel frequency of the ECG transmitter unit 1. The output of 146 is mixed by the mixer 147 with the output of the local oscillator 148. The local oscillator 148 is crystal controller to a frequency exactly 10.7 megahertz above the RF channel frequency of the transmitter. The output of the mixer passes through the 10.7 megahertz intermediate frequency (IF) filter 149. The output of 149 is amplified by the IF amplifier 150 and fed to the discriminator circuit 151. The output of 151 goes through a buffer 152 and a Schmitt trigger 153 to a monostable multivibrator 154. The output 155 of 154 is the serial data as shown in FIG. 12. This serial data is processed by sync separator and timing circuits consisting of 160, 161, 162, 163 and 164 to generate a data bit clock 159 and a frame sync clock 158. These clock signals, together with the frame decoder circuit 170, is used to lock in each data frame of each data cluster into the 40-bit serial-in-parallel-out shift register 157. The output of the decoder circuit 170 is also used to latch each ECG lead data byte and each status byte into the latches 165 through 169 as shown in FIG. 14.

Since certain changes may be made in the above method and embodiment without departing from the scope of the invention herein involved, it is intended that all matter contained in the above description or shown in the accompanying drawings shall be interpreted as illustrative and not in a limiting sense. For example, it will be understood by one skilled in the art that the ECG unit could communicate its data to the stationary location marker which in turn could retransmit the location data and the ECG unit data to the stationary receiver using the circuitry described herein. Further, the invention need not be limited to ECG signals but may be used to transmit other physiological data in addition to or in lieu of the ECG data.

I claim:

1. A patient location system for locating a patient within a plurality of bounded spaces comprising:
    stationary location marker means fixed with respect to a bounded space for generating a location code;
    patient identification means affixed to a patient for generating a patient identification signal;
    low power link for communicating the location code from the stationary location marker means to the patient identification means only when the patient identification means is in the bounded space;
    a physiological monitor means for monitoring a physiological signal from the patient;
    first transmitter means affixed to the patient and communicating with the patient identification means and the physiological monitor means for transmitting the location code, the patient identification signal, and the physiological signal when the stationary location marker means is in communication with the patient identification means through the low power link; and
    stationary receiver means for receiving the location code and patient identification signal whereby the patient identification means may be associated with the location means.

2. The patient location system of claim 1 wherein the low power link means is comprised of an infrared transmitter and receiver means for communicating by infrared light.

3. The patient location system as recited in claim 1 wherein the physiological signal is a continuous signal and wherein the first transmitter provides continuous transmission of the physiological signal.

4. The biotelemetry and patient location system of claim 1 wherein the patient identification signal is encoded in the carrier frequency of the first transmitter means.

5. A bio-telemetry and patient location system for monitoring physiological signals of a patient within a bounded space which comprises:
    stationary location marker means for transmitting a presettable location code on a low power communication link, wherein said stationary location marker is fixed within a bounded space and the power level within the bounded space is above a signal threshold;
    mobile receiver means attached to the patient for receiving said location code signal only if it is above the signal threshold and including a physiological monitor means for monitoring a physiological signal from the patient;
    transmitter means communicating with the mobile receiver means for combining the location code signal received by the mobile receiver means with the physiological signal and transmitting the combined physiological signals and location code signal; and
    stationary receiver means for receiving the transmitted combined physiological signals and location code.

6. The bio-telemetry and patient location system of claim 5 wherein the transmitter means includes means for transmitting the combined physiological signal and location code on a radio frequency channel, and wherein the stationary receiver means includes means to identify the radio frequency channel of the received combined physiological signal and corresponding location code.

7. The bio-telemetry and patient location system of claim 5 wherein the location code signal is transmitted serially on an infrared light beam.

8. The bio-telemetry and patient location system of claim 5 wherein the mobile receiver means includes a patient activated distress switch means activated by the patient for producing a distress signal, and wherein the transmitter means includes means for combining the distress signal with the location code wherein the combined distress signal and location code signal and physiological signal is transmitted by the transmitter means.

9. The bio-telemetry and patient location system of claim 5 including an electrode status detector means comprising:
    impedance detector means for detecting electrode impedance outside of a predetermined range; and
    light emitting diode means for producing a visible indication of a high impedance detected by the impedance detector means.

* * * * *